United States Patent [19]

Nakayama et al.

[11] Patent Number: 4,508,562
[45] Date of Patent: Apr. 2, 1985

[54] BENZYLSULFINYL PYRIDINE-N-OXIDES AND THEIR HERBICIDAL METHOD OF USE

[75] Inventors: Koji Nakayama, Osaka; Ryo Yoshida, Hyogo; Hiroshi Matsumoto, Osaka, all of Japan

[73] Assignee: Sumitomo Chemical Company, Limited, Osaka, Japan

[21] Appl. No.: 498,990

[22] Filed: May 27, 1983

[30] Foreign Application Priority Data

May 28, 1982 [JP] Japan ................................. 57-91929
Nov. 24, 1982 [JP] Japan ............................... 57-206310

[51] Int. Cl.³ ................... C07D 213/71; A01N 43/40
[52] U.S. Cl. ....................................... 71/94; 546/295; 546/294
[58] Field of Search ................... 546/295, 294; 71/94

[56] References Cited

U.S. PATENT DOCUMENTS 4,019,893 4/1977 Plant et al. ........................... 71/94

FOREIGN PATENT DOCUMENTS 36638 9/1981 European Pat. Off. ............... 71/94

*Primary Examiner*—Alan L. Rotman
*Attorney, Agent, or Firm*—Sughrue, Mion, Zinn, Macpeak and Seas

[57] ABSTRACT

Benzylsulfinyl pyridine-N-oxides represented by the formula:

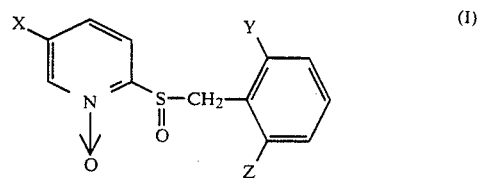

wherein X is a chlorine atom or a bromine atom; and Y and Z, which may be the same or different, are each a chlorine atom or a fluorine atom, is disclosed. A process for producing the same, and a herbicide containing the same as an active ingredient are also disclosed.

4 Claims, No Drawings

BENZYLSULFINYL PYRIDINE-N-OXIDES AND THEIR HERBICIDAL METHOD OF USE

This invention relates to benzylsulfinyl pyridine-N-oxide represented by the formula:

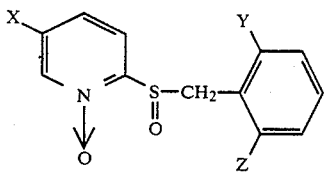

wherein X is a chlorine atom or a bromine atom; and Y and Z, which may be the same or different, are each a chlorine atom or a fluorine atom, a process for producing the same, and a herbicide containing the same as an active ingredient.

It is disclosed in U.S. Pat. No. 4,019,893 and European Patent Publication No. 0036638A2 that some pyridine-N-oxides, e.g., 2-(2,6-dichlorobenzylsulfinyl)pyridine-N-oxide, 5-bromo-2-(2,6-dichlorobenzylsulfonyl)-pyridine-N-oxide, etc., are useful as active ingredients of herbicides. However, it cannot be said that these known compounds are always satisfactory as herbicides.

The compounds of this invention have herbicidal activity against various weeds which are of problem in the pre-emergence soil treatment of upland fields, such as broad-leafed weeds (e.g., wild buckwheat (*Polygonum convolvulus*), chickweed (*Stellaria media*), radish (*Raphanus sativus*), wild mustard (*Sinapis arvensis*), hemp sesbania (*Sesbania exaltata*), sicklepod (*Cassia obtusifolia*), velvetleaf (*Abutilon theophrasti*), prickly sida (*Sida spinosa*), bedstraw (*Galium aparine*), ivyleaf morningglory (*Ipomoea hederacea*), tall morningglory (*Ipomoea purpurea*), cocklebur (*Xanthium strumarium*), corn marigold (*Chrysanthemum segetum*), etc.); gramineous weeds (e.g., Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), black grass (*Alopecurus myosuroides*), oat (*Avena sativa*), wild oat (*Avena fatua*), Johnsongrass (*Sorghum halepense*), quackgrass (*Agropyron repens*), bermudagrass (*Cynodon dactylon*), fall panicum (*Panicum dichotomiflorum*), etc.); Commelina weeds (e.g., dayflower (*Commelina communis*), etc.); sedge weeds (e.g., *Cyperus esculentus*, etc.); and the like. Some of the compounds of this invention are not substantially phytotoxic against main crops such as soybeans (*Glycine max*), cotton (*Gossypium sp.*), barley (*Hordeum vulgare*), rice (*Oryza sativa*), etc.

Further, the compounds of this invention have herbicidal activity against various weeds which are of problem in paddy fields, such as gramineous weeds (e.g., barnyardgrass (*Echinochloa oryzicola*), etc.); broad-leafed weeds (e.g., false pimpernel (*Lindernia procumbens*), spike-flowered rotala (*Rotala indica*), etc.); sedge weeds (e.g., bulrush (*Scirpus juncoides*), slender spike-rush (*Eleocharis acicularis*), etc.); weeds in paddy field (e.g., Japanese ribbon wapato (*Sagittaria pygmaea*), etc.); and the like, with being not substantially phototoxic against rice (*Oryza sativa*).

The compound of this invention can be produced by oxidizing benzylthiopyridine-N-oxide represented by the formula:

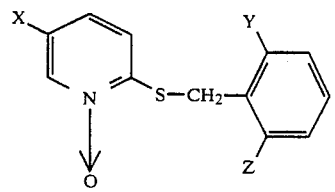

wherein X, Y and Z are the same as defined above, with oxidizing agents.

Suitable examples of the oxidizing agent which can be used include inorganic peroxides such as hydrogen peroxide, sodium metaperiodate, etc.; aliphatic peroxides such as peracetic acid, etc.; aromatic peroxides such as metachloroperbenzoic acid, etc.; and the like.

Use of solvents are not essential, but when used, the solvents varies depending upon the kind of the oxidizing agent. For example, it is suitable to use water, glacial acetic acid, acetone, etc., for hydrogen peroxide; and halogenated hydrocarbons (e.g., chloroform, methylene chloride, etc.) or ethers (e.g., diethyl ether, dioxane, etc.) for the aromatic peroxides, respectively. Further, when the aliphatic peroxides is used, it is suitable to use the oxidizing agent per se in an excessive amount.

The oxidizing agent is usually used in an amount of 0.5 to 1.5 equivalents, preferably 0.95 to 1.2 equivalents, to the benzylthiopyridine-N-oxide. The reaction temperature which can be employed ranges from the freezing point to boiling point of the solvent used, preferably from 0° C. to the boiling point of the solvent. The reaction time which can be employed ranges from 30 minutes to 10 hours. After completion of the reaction, the reaction mixture is treated in the conventional methods. When desired, the product is purified by recrystallization, column chromatography, or the like.

The benzylthiopyridine-N-oxide of the formula (II) can be obtained according to, for example, a method as disclosed in European Patent Publication No. 0036638A2.

The compounds of this invention are explained by reference to the following Examples.

EXAMPLE 1

Production of Compound (1)

3.2 g of 5-chloro-2-(2,6-dichlorobenzylthio)pyridine-N-oxide was dissolved in 50 ml of chloroform, and a solution of 2.5 g of metachloroperbenzoic acid (content: 70%) dissolved in 30 ml of chloroform was added dropwise thereto at 5° to 10° C. over 10 minutes. The mixture was stirred at 5° to 10° C. for an additional 2 hours. The resulting mixture was washed twice with potassium carbonate solution and dried over magnesium sulfate. The chloroform was evaporated and the residue was recyrstallized from 1:1 benzene-hexane to obtain 3.2 g of 5-chloro-2-(2,6-dichlorobenzylsulfinyl)pyridine-N-oxide (Compound (1)). Yield, 95%. M.P., 176.5°–177.5° C.

H-NMR in $CDCl_3$ (in which tetramethylsilane was used as a standard): δ8.2 ppm (multiplet,1H), δ7.6–7.2 ppm (multiplet, 5H), δ5.1 ppm (quartet, 2H).

EXAMPLE 2

Production of Compound (2)

2.3 g of 5-bromo-2-(2,6-dichlorobenzylthio)pyridine-N-oxide was dissolved in 50 ml of chloroform, and a solution of 1.6 g of metachloroperbenzoic acid (content: 70%) dissolved in 30 ml of chloroform was added dropwise thereto at 5° to 10° C. over 10 minutes. The mixture was stirred at 5° to 10° C. for an additional 2 hours. The resulting mixture was washed twice with potassium carbonate solution and dried over magnesium sulfate. The chloroform was evaporated, and the residue was recrystallized from benzene to obtain 2.0 g of 5-bromo-2-(2,6-dichlorobenzylsulfinyl)pyridine-N-oxide (Compound (2)). Yield, 83%. M.P., 187.5°–188.5° C.

H-NMR in CDCl$_3$ (in which tetramethylsilane was used as a standard): δ8.3 ppm (multiplet, 1H), δ7.5–7.1 ppm (multiplet, 5H), δ5.0 ppm (quartet, 2H).

Typical examples of the compounds of this invention which can be produced in the similar manner as above are listed in Table 1 below.

TABLE 1

| Compound No. | X  | Y  | Z  | Physical Constant    |
|--------------|----|----|----|----------------------|
| (1)          | Cl | Cl | Cl | M.P., 176.5–177.5° C.|
| (2)          | Br | Cl | Cl | M.P., 187.5–188.5°C. |
| (3)          | Cl | Cl | F  | M.P., 175.5–176.5°C. |
| (4)          | Br | Cl | F  | M.P., 170–171° C.    |
| (5)          | Cl | F  | F  | M.P., 156–157°C.     |
| (6)          | Br | F  | F  | M.P., 154–155°C.     |

When the compound of this invention is used as an active ingredient of herbicide, it can be formulated into various composition-forms such as emulsifiable concentrates, wettable powders, suspensions, dusts, granules, etc., by incorporating conventional solid carriers, liquid carriers, surfactants, or other agriculturally acceptable adjuvants. A suitable content of the compound of this invention in the composition is 0.5 to 90% by weight, preferably 1 to 80% by weight.

Suitable examples of the solid carriers which can be used include kaolin clay, bentonite, talc, diatomaceous earth, Jeeklite, synthetic hydrated silicon dioxide, and so on. Suitable examples of the liquid carriers which can be used include aromatic hydrocarbons (e.g., xylene, methylnaphthalene, etc.), ketones (e.g., cyclohexanone, isophorone, etc.), halogenated hydrocarbons (e.g., chlorobenzene, dichloroethane, etc.), dimethylformamide, cellosolve, ethylene glycol, water, and so on. Suitable examples of the surfactants which can be used for emulsification, dispersion or spreading include nonionic surfactants (e.g., polyoxyethylene alkyl ethers, polyoxyethylene alkylaryl ethers, polyoxyethylene styrylaryl ethers, polyoxyethylene fatty acid esters, polyoxyethylene sorbitan fatty acid esters, oxyethyleneoxypropylene blocked polymers, etc.), anionic surfactants (e.g., alkyl sulfates, alkyl sulfonates, dialkyl sulfosuccinates, alkylaryl sulfonates, etc.), and so on.

Suitable examples of the other agriculturally acceptable adjuvants which can be used include lignin sulfonates, alginate, polyvinyl alcohol, cellulose, PAP (isopropyl acid phosphate), BHT (2,6-di-t-butyl-4-methylphenol), and so on.

Typical compositions are explained by reference to the following Formulation Examples. In the Formulation Examples, all parts are by weight.

FORMULATION EXAMPLE 1

80 parts of Compound (2), (4) or (5), 5 parts of polyoxyethylene alkylaryl ether and 15 parts of synthetic hydrated silicon dioxide are thoroughly pulverized and mixed to obtain a wettable powder.

FORMULATION EXAMPLE 2

3 parts of Compound (1), (3) or (5), 10 parts of polyoxyethylene alkylaryl ether, 5 parts of alkylaryl sulfonate and 82 parts of isophorone are thoroughly mixed to obtain an emulsifiable concentrate.

FORMULATION EXAMPLE 3

1 part of Compound (1), (3) or (6), 1 part of synthetic hydrated silicon dioxide, 5 parts of sodium lignin sulfonate and 93 parts of kaolin clay are thoroughly pulverized and mixed and then well kneaded with water. The resulting mixture is granulated and dried to obtain granules.

FORMULATION EXAMPLE 4

3 parts of Compound (2), (4) or (6), 0.5 part of isopropyl acid phosphate, 66.5 parts of kaolin clay and 30 parts of talc are thoroughly pulverized and mixed to obtain dusts.

FORMULATION EXAMPLE 5

20 parts of Compound (1), (3) or (5) is mixed with 60 parts of an aqueous solution containing 3% by weight of polyoxyethylene sorbitan monooleate, and the mixture is pulverized in a wet manner until the particle size became 3μ or less. The resulting mixture was mixed with 20 parts of an aqueous solution containing 3% by weight of sodium alginate as a dispersion stabilizer to obtain a suspension.

The thus obtained emulsifiable concentrate, wettable powder, suspension and the like are, in general, subjected to foliar treatment or soil treatment upon diluting with water. On the other hand, the granules, dusts and the like are subjected to the same treatment as they are. In order to strengthen the activity as a herbicide, the compound of this invention can be applied together with other herbicide with or without mixing therewith, and in some cases, a synergistic effect can be expected. Further, the compound of this invention can be mixed or used together with insecticides, acaricides, nematocides, fungicides, plant growth regulators, fertilizers, soil improvers, etc.

The compound of this invention can also be used as an active ingredient of herbicide in orchards, pasture lands, turf lands, forests and various non-agricultural lands in addition to upland fields and paddy fields.

In any case of the foliar treatment and soil treatment, the application amount of the compound of this invention can be altered within a considerably wide range. But it is usually 0.1 to 200 g, preferably 0.2 to 100 g, per are calculated as an amount of active ingredient.

The application concentration is 0.02 to 2% by weight in the water-diluted solutions of emulsifiable concentrate, wettable powder, suspension, etc. The application amount and concentration of the compound can be altered depending upon the kind of composition-form, the application place, the application method, the application time, the kind of crop, the kind of weed, the degree of damage by weeds, the climate condition, etc, regardless the range as defined above.

In order to demonstrate that the compound of this invention is useful as an active ingredient of herbicide, the invention is explained by reference to the following Test Examples. In the Test Examples, the phytotoxicity against crops and the herbicidal activity against weeds were evaluated on a scale of 0 to 5 grades by weighing a fresh weight of the aerial parts of the remaining withered plant and calculating a ratio (%) to that of the untreated plot. The evaluation was made in accordance with the criterion as shown in Table 2 below.

TABLE 2

| Evaluation Grade | Ratio (%) of Fresh Weight to That of Untreated Plot | |
|---|---|---|
| | Herbicidal Activity against Weeds | Phytotoxicity against Crops |
| 0 | 91~ | 91~ |
| 1 | 71~90 | 71~90 |
| 2 | 41~70 | 51~70 |
| 3 | 11~40 | 31~50 |
| 4 | 4~10 | 11~30 |
| 5 | 0~3 | 0~10 |

Comparative Compounds used in the Test Examples are listed in Table 3 below.

TABLE 3

| Compound No. | Chemical Structure | Physical Constant (melting point) (°C.) |
|---|---|---|
| (a) | [pyridine N-oxide, 2-SO-CH$_2$-(2,6-dichlorophenyl)] | 135-137 |
| (b) | [pyridine N-oxide, 2-SO$_2$-CH$_2$-(2,5-dimethylphenyl)] | 152-154 |
| (c) | [pyridine N-oxide, 2-SO$_2$-CH(CH$_3$)-(2,5-dimethylphenyl)] | 162-163 |
| (d) | [4-CH$_3$ pyridine N-oxide, 2-SO-CH$_2$-(2,5-dimethylphenyl)] | 124-125 |
| (e) | [4-CH$_3$ pyridine N-oxide, 2-SO$_2$-CH$_2$-(2,5-dimethylphenyl)] | 134-135 |
| (f) | [5-CH$_3$ pyridine N-oxide, 2-SO$_2$-CH$_2$-(2,5-dimethylphenyl)] | 154.5-156 |
| (g) | [5-Br pyridine N-oxide, 2-SO$_2$-CH$_2$-(2,5-dimethylphenyl)] | 185-186 |
| (h) | [5-Br pyridine N-oxide, 2-SO$_2$-CH$_2$-(2,6-dichlorophenyl)] | 207-209 |
| (i) | [5-CH$_3$ pyridine N-oxide, 2-SO-CH$_2$-(2,6-dichlorophenyl)] | 153-154 |

Compounds (a) to (c): Compounds as disclosed in U.S. Pat. No. 4,019,893
Compounds (d) to (h): Compounds as disclosed in European Patent Publication No. 0036638A2
Compound (i): Compound as produced for comparison

TEST EXAMPLE 1

Pre-Emergence Soil Treatment in Paddy Field

A plastics pot having an inside diameter of 8 cm and a height of 10 cm was packed with a soil for paddy field and predetermined amounts of seeds of barnyardgrass (*Echinochloa oryzicola*), broad-leafed weeds (false pimpernel (*Lindernia procumbens*) and spike-flowered rotala (*Rotala indica*) and bulrush (*Scirpus juncoides*) were sown, followed by covering with a soil. Then, water was poured into the pot to a water depth of 3 cm. The resulting pot was allowed to stand in a greenhouse for one day, and a solution prepared by diluting a predetermined amount of an emulsifiable concentrate formulated in accordance with Formulation Example 2 with 5 ml of water was added dropwise onto the water surface.

The pot was allowed to stand in the greenhouse for an additional 20 days to evaluate the herbicidal activity. The results obtained are shown in Table 4 below.

TABLE 4

| Compound No. | Application Amount of Active Ingredient (g/a) | Herbicidal Activity | | |
|---|---|---|---|---|
| | | Barnyard-grass | Broad-Leafed Weeds | Bulrush |
| (1) | 20 | 5 | 5 | 5 |
| | 5 | 5 | 5 | 5 |
| (2) | 20 | 5 | 5 | 5 |
| | 5 | 5 | 5 | 5 |
| (3) | 20 | 5 | 5 | 5 |
| | 5 | 5 | 5 | 4 |
| (4) | 20 | 5 | 5 | 5 |
| | 5 | 5 | 5 | 4 |
| (5) | 20 | 5 | 5 | 5 |
| | 5 | 5 | 5 | 5 |
| (6) | 20 | 5 | 5 | 5 |
| | 5 | 5 | 5 | 5 |
| (a) | 20 | 4 | 4 | 3 |
| | 5 | 3 | 3 | 2 |
| (b) | 20 | 3 | 2 | 1 |
| | 5 | 2 | 0 | 1 |
| (c) | 20 | 2 | 0 | 0 |
| | 5 | 0 | 0 | 0 |
| (d) | 20 | 5 | 3 | 2 |
| | 5 | 3 | 2 | 1 |
| (e) | 20 | 5 | 4 | 2 |
| | 5 | 3 | 3 | 2 |
| (f) | 20 | 2 | 0 | 2 |
| | 5 | 1 | 0 | 2 |
| (g) | 20 | — | 3 | 4 | 5 |
| | 5 | 2 | 2 | 3 |
| (h) | 20 | 3 | 4 | 3 |
| | 5 | 1 | 4 | 2 |
| (i) | 20 | 5 | 3 | 3 |
| | 5 | 4 | 2 | 2 |

TEST EXAMPLE 2

Foliar and Soil Treatment in Paddy Field

A 1/5,000 are Wagner pot was packed with a soil for paddy field, and predetermined amounts of seeds of barnyardgrass (*Echinochloa oryzicola*), bulrush (*Scirpus juncoides*) and broad-leafed weeds (false pimpernel (*Lindernia procumbens*) and spike-flowered rotala (*Rotala indica*)) and hibernated buds of slender spikerush (*Eleocharis acicularis*) were incorporated into the soil at a depth of 3 cm from the soil surface. Water was then added to the pot to a water depth of 4 cm. Then, 3-leaf stage rice (*Oryza sativa*) was transplanted. The plants were grown in a greenhouse for 5 days, and when the weeds had germinated, a solution prepared by diluting a predetermined amount of an emulsifiable concentrate formulated in accordance with Formulation Example 2 with 10 ml of water was added dropwise onto the water surface. 20 days after the addition, the herbicidal activity and the phytotoxicity against the rice were evaluated. The results obtained are shown in Table 5 below.

TABLE 5

| Compound No. | Application Amount of Active Ingredient (g/a) | Phytotoxicity against Crop Rice | Herbicidal Activity | | | |
|---|---|---|---|---|---|---|
| | | | A | B | C | D |
| (1) | 10 | 1 | 5 | 5 | 5 | 5 |
| | 5 | 0 | 5 | 5 | 5 | 5 |
| 2) | 10 | 1 | 5 | 5 | 5 | 5 |
| | 5 | 1 | 4 | 5 | 5 | 5 |
| (3) | 10 | 1 | 5 | 5 | 5 | 5 |

TABLE 5-continued

| Compound No. | Application Amount of Active Ingredient (g/a) | Phytotoxicity against Crop Rice | Herbicidal Activity | | | |
|---|---|---|---|---|---|---|
| | | | A | B | C | D |
| (5) | 10 | | | | | |
| | 5 | 0 | | | | |
| (6) | 10 | | | | | |
| | 5 | 0 | | | | |
| (a) | 10 | | | | | |
| | 5 | 0 | | | | |
| (c) | 10 | 0 | | | | |
| | 5 | | | | | |
| (h) | 10 | 0 | | | | |
| | 5 | | | | | |
| (i) | 10 | 0 | | | | |
| | 5 | | | | | |

A: Barnyardgrass
B: Broad-Leafed Weeds
C: Slender Spikerush
D: Bulrush

TEST EXAMPLE 3

Pre-Emergence Soil Incorporation Treatment in Upland Field

A cylindrical plastics pot having a diameter of 10 cm and a height of 10 cm was packed with a soil for upland field and predetermined amounts of seeds of Japanese millet (*Echinochloa frumentacea*), oat (*Avena sativa*), tall morningglory (*Ipomoea purpurea*) and velvetleaf (*Abutilon theophrasti*) and tubers of yellow nutsedge (*Cyperus esculentus*) were sown, followed by covering with a soil. Then, a solution prepared by diluting an emulsifiable concentrate formulated in accordance with Formulation Example 2 with water was applied onto the surface of the soil in a spray volume of 10 l per are by means of a small-sized sprayer. Thereafter, the surface portion of soil up to a depth of 4 cm was thoroughly incorporated. The plants were then grown in a greenhouse for 20 days, and the herbicidal activity was evaluated. The results obtained are shown in Table 6 below.

TABLE 6

| Compound No. | Application Amount of Active Ingredient (g/a) | Herbicidal Activity | | | | |
|---|---|---|---|---|---|---|
| | | A | B | C | D | E |
| (1) | 30 | 5 | | | | |
| | 10 | 4 | | | | |
| (2) | 30 | 5 | | | | |
| | 10 | 4 | | | | |
| (3) | 30 | 5 | | | | |
| | 10 | 5 | 4 | | | |
| (4) | 30 | 5 | | | | |
| | 10 | 4 | | | | |
| (5) | 30 | 5 | | | | |
| | 10 | 5 | | | | |
| (6) | 30 | 5 | | | | |
| | 10 | 5 | | | | |

A: Japanese millet
B: Oat
C: Tall Morningglory
D: Velvetleaf
E: Yellow nutsedge

TEST EXAMPLE 4

Soil Treatment in Upland Field

A flat (area: 33×23 cm², height: 11 cm) was packed with a soil for upland field, and predetermined amounts of seeds of soybeans (*Glycine max*), cotton (*Gosspium* sp.), burmudagrass (*Cynodon dactylon*), goosegrass (*Eleusine indica*), barnyardgrass (*Echinochloa crus-galli*), green foxtail (*Setaria viridis*) and fall panicum (*Panicum dichotomiflorum*) were sown, followed by covering with the soil to a thickness of 1 to 2 cm. A solution prepared by diluting a predetermined amount of an emulsifiable concentrate formulated in accordance with Formulation Example 2 with water was applied onto the surface of the soil in a proportion of 5 l per are by means of a small-sized sprayer. After the application, the plants were grown in a greenhouse for 20 days, and the herbicidal activity was evaluated. The results obtained are shown in Table 7 below.

TABLE 7

| Compound No. | Application Amount of Active Ingredient (g/a) | Herbicidal Activity | | | | | | |
|---|---|---|---|---|---|---|---|---|
| | | A | B | C | D | E | F | G |
| (1) | 1 | 0 | 0 | 5 | 5 | 5 | 5 | 5 |
| | 0.5 | 0 | 0 | 4 | 4 | 3 | 4 | 4 |
| (3) | 1 | 0 | 0 | 5 | 5 | 5 | 5 | 5 |
| | 0.5 | 0 | 0 | 5 | 4 | 4 | 4 | 5 |
| (4) | 1 | 0 | 0 | 5 | 5 | 4 | 5 | 5 |
| | 0.5 | 0 | 0 | 4 | 3 | 4 | 4 | 5 |
| (5) | 1 | 0 | 0 | 5 | 5 | 5 | 5 | 5 |
| | 0.5 | 0 | 0 | 4 | 5 | 4 | 4 | 5 |
| (6) | 1 | 0 | 0 | 5 | 5 | 4 | 4 | 5 |
| | 0.5 | 0 | 0 | 4 | 3 | 4 | 3 | 4 |
| (a) | 1 | 0 | 0 | 3 | 4 | 3 | 4 | 4 |
| | 0.5 | 0 | 0 | 1 | 2 | 1 | 2 | 2 |
| (h) | 1 | 0 | 0 | 3 | 2 | 0 | 1 | 2 |
| | 0.5 | 0 | 0 | 0 | 0 | 0 | 0 | 1 |

A: Soybeans
B: Cotton
C: Bermudagrass
D: Goosegrass
E: Barnyardgrass
F: Green Foxtail
G: Fall Panicum

TEST EXAMPLE 5

Soil Treatment in Upland Field

A flat (area: 33×23 cm², height: 11 cm) was packed with a soil for upland field, and predetermined amounts of seeds of barley (*Hordeum vulgare*), quackgrass (*Agropyron repens*), wild oat (*Avena fatua*), black grass (*Alopecurus myo suroides*) and annual bluegrass (*Poa annua*) were sown, followed by covering with a soil to a thickness of 1 to 2 cm. A solution prepared by diluting a predetermined amount of an emulsifiable concentrate formulated in accordance with Formulation Example 2 with water was applied onto the surface of the soil in a spray volume of 5 l per are by means of a sprayer. After the application, the plants were grown in a greenhouse for 27 days, and the herbicidal activity was evaluated. The results obtained are shown in Table 8 below.

TABLE 8

| Compound No. | Application Amount of Active Ingredient (g/a) | Herbicidal Activity | | | | |
|---|---|---|---|---|---|---|
| | | A | B | C | D | E |
| (3) | 3 | 1 | 5 | 5 | 5 | 5 |
| | 1.5 | 0 | 4 | 4 | 5 | 5 |
| (5) | 3 | 0 | 4 | 5 | 5 | 5 |
| | 1.5 | 0 | 4 | 4 | 5 | 5 |
| (a) | 3 | 1 | 1 | 2 | 4 | 4 |
| | 1.5 | 0 | 0 | 0 | 3 | 3 |
| (h) | 3 | 0 | 0 | 1 | 2 | 3 |
| | 1.5 | 0 | 0 | 0 | 1 | 1 |

A: Barley
B: Quackgrass
C: Wild Oat
D: Black Grass
E: Annual Bluegrass

What is claimed is:

1. A compound of the formula:

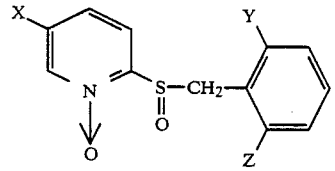

wherein X is a chlorine atom or a bromine atom; and Y and Z, which may be the same or different, are each a chlorine atom or a fluorine atom.

2. 5-Chloro-2-(2-chloro-6-fluorobenzylsulfinyl)pyridine-N-oxide.

3. A herbicidal composition which comprises as an active ingredient a herbicidally effective amount of the compound according to claim 1, and an inert carrier.

4. A method for controlling weeds which comprises applying a herbicidally effective amount of the compound according to claim 1 to the field for cultivating soybeans, cotton, barley or rice.

* * * * *